United States Patent
Bauss et al.

(10) Patent No.: US 9,884,155 B2
(45) Date of Patent: Feb. 6, 2018

(54) FILM-BASED PROTECTIVE MECHANISM

(75) Inventors: Markus Bauss, Lengdorf (DE); Robert Licha, Oberschleissheim (DE); Ulrich Moosheimer, Hohenkammer (DE); Robert Unglert, München (DE)

(73) Assignee: SCHREINER GROUP GmbH & Co. KG, Oberschleissheim (DE)

(*) Notice: Subject to any disclaimer, the term of this patent is extended or adjusted under 35 U.S.C. 154(b) by 1403 days.

(21) Appl. No.: 11/918,116

(22) PCT Filed: May 2, 2005

(86) PCT No.: PCT/EP2005/004735
§ 371 (c)(1),
(2), (4) Date: Oct. 9, 2007

(87) PCT Pub. No.: WO2006/105807
PCT Pub. Date: Oct. 12, 2006

(65) Prior Publication Data
US 2009/0054847 A1    Feb. 26, 2009

(30) Foreign Application Priority Data
Apr. 6, 2005  (DE) .......................... 10 2005 015 801

(51) Int. Cl.
*A61M 5/32*    (2006.01)
(52) U.S. Cl.
CPC ........ *A61M 5/3216* (2013.01); *A61M 5/3204* (2013.01)
(58) Field of Classification Search
CPC .. A61M 5/3202; A61M 5/3204; A61M 5/321; A61M 5/3216; A61M 5/3219; A61M 5/50; A61M 5/5086; A61M 2005/3217
(Continued)

(56) References Cited

U.S. PATENT DOCUMENTS 2,712,315 A * 7/1955 Rice ................................ 604/60
3,968,876 A * 7/1976 Brookfield .................... 206/365
(Continued)

FOREIGN PATENT DOCUMENTS

DE    41 07 042    9/1992
DE    38 74 397    10/1994
(Continued)

OTHER PUBLICATIONS

Examination Report in DE 10 2005 015 801.3 (with English translation of relevant parts).
(Continued)

Primary Examiner — Kami A Bosworth
(74) Attorney, Agent, or Firm — Collard & Roe, P.C.

(57) ABSTRACT

The invention relates to a method for producing a device containing a needle that poses an injury risk, which is equipped with a protective mechanism. The method comprises the following steps, which may be carried out in any order: a) provision of at least one film, b) connection of the film to a protective device to form a protective mechanism, and c) fixing of the protective mechanism to the device, whereby at least part of the surface of the film can be fixed directly or indirectly to the device. The invention also relates to a protective mechanism for a device containing a needle that poses an injury risk, the device comprising at least one film, in addition to an assembly of protective mechanisms, in which the protective mechanisms are directly or indirectly connected.

46 Claims, 3 Drawing Sheets

Figure 1:
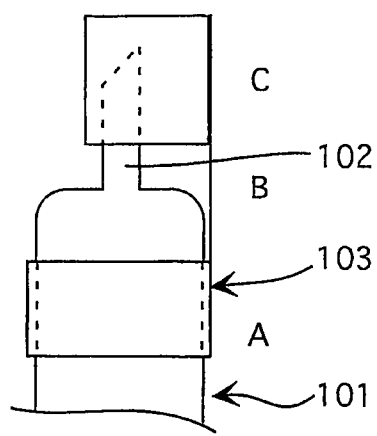

(58) Field of Classification Search
USPC .......... 604/110, 111, 189, 192, 263; 206/365
See application file for complete search history.

(56) References Cited

U.S. PATENT DOCUMENTS

| | | | |
|---|---|---|---|
| 4,643,722 A * | 2/1987 | Smith, Jr. ..................... | 604/192 |
| 4,704,177 A * | 11/1987 | Vaillancourt ................. | 156/226 |
| 4,735,618 A | 4/1988 | Hagen | |
| 4,758,229 A * | 7/1988 | Doerschner ......... | A61M 5/3216 |
| | | | 206/365 |
| 4,883,469 A | 11/1989 | Glazier | |
| 4,886,503 A * | 12/1989 | Miller ................. | A61M 5/3216 |
| | | | 604/192 |
| 4,932,946 A * | 6/1990 | Shields ............... | A61M 5/3202 |
| | | | 604/198 |
| 5,383,862 A | 1/1995 | Berndt et al. | |
| 5,395,319 A | 3/1995 | Hirsch et al. | |
| 5,462,531 A | 10/1995 | Novacek et al. | |
| 5,506,015 A * | 4/1996 | Frederiksen et al. ........ | 428/41.8 |
| 5,624,402 A | 4/1997 | Imbert | |
| 5,643,219 A * | 7/1997 | Burns .......................... | 604/192 |
| 5,658,256 A * | 8/1997 | Shields ........................ | 604/192 |
| 5,829,194 A * | 11/1998 | Weder .............................. | 47/72 |
| 5,833,653 A | 11/1998 | Vetter et al. | |
| 5,879,337 A | 3/1999 | Kuracina et al. | |
| 6,261,264 B1 * | 7/2001 | Tamaro ......................... | 604/198 |
| 6,328,713 B1 * | 12/2001 | Hollister ....................... | 604/192 |
| 6,485,460 B2 * | 11/2002 | Eakins et al. ................. | 604/111 |
| 6,726,649 B2 * | 4/2004 | Swenson .............. | A61B 17/205 |
| | | | 206/365 |
| 6,796,968 B2 | 9/2004 | Ferguson et al. | |
| 7,556,149 B2 * | 7/2009 | Erickson et al. ............. | 206/366 |
| 2001/0039404 A1 | 11/2001 | Rolle | |
| 2002/0065488 A1 | 5/2002 | Suzuki | |
| 2003/0114797 A1 * | 6/2003 | Vaillancourt et al. ........ | 604/171 |
| 2003/0121812 A1 * | 7/2003 | Sprieck et al. ............... | 206/365 |
| 2008/0200881 A1 * | 8/2008 | Emmott et al. ............... | 604/192 |

FOREIGN PATENT DOCUMENTS

| | | | |
|---|---|---|---|
| DE | 196 38 940 | 4/1998 | |
| DE | 100 28 829 | 12/2001 | |
| DE | 201 21 260 | 8/2002 | |
| DE | 696 21 994 | 10/2002 | |
| DE | 103 16 237 | 11/2004 | |
| EP | 0 288 443 | 10/1988 | |
| EP | 0 765 651 | 4/1997 | |
| JP | 2002-191695 | 7/2002 | |
| WO | WO 94/24263 | 10/1994 | |
| WO | WO 99/36114 | 7/1999 | |
| WO | WO 00/62848 | * 10/2000 | ............. A61M 5/50 |

OTHER PUBLICATIONS

International Search Report.
English Translation of an Examination Report dated May 17, 2011 in Corresponding Japanese Patent Application No. P2008-504625.

* cited by examiner

Fig. 9
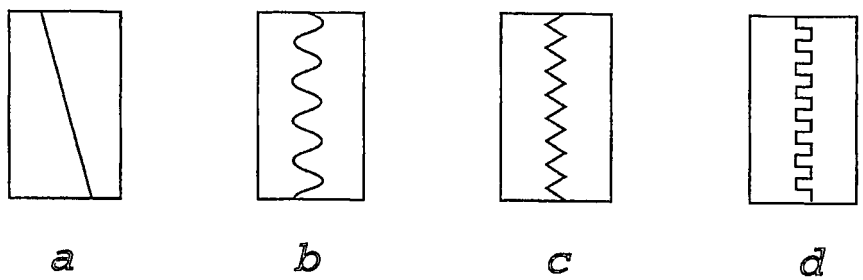
a  b  c  d
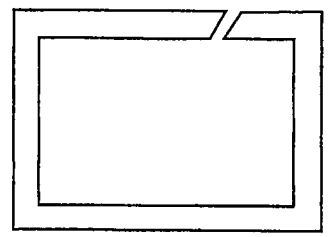
Fig. 10
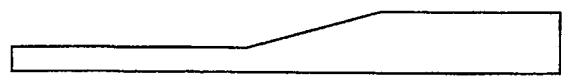
Fig. 11

FILM-BASED PROTECTIVE MECHANISM

CROSS REFERENCE TO RELATED APPLICATIONS

Applicants claim priority under 35 U.S.C. § 119 of German Application No. 10 2005 015 801.3 filed on Apr. 6, 2005. Applicants also claim priority under 35 U.S.C. § 365 of PCT/EP2005/004735 filed on May 2, 2005. The international application under PCT article 21(2) was not published in English.

The present invention relates to a protective mechanism for syringes, needles, or other devices having pointed or sharp objects. Specifically, it relates to a protective mechanism for such devices in the medical/pharmaceutical sector of use.

Numerous injuries in the clinical or other medical sector are caused by accidental contact with sharp and/or pointed treatment devices, primarily syringe needles or scalpels. Such injuries are particularly hazardous for the persons affected because there is often an infection risk involved, for example in the case of direct penetration of bodily fluids of patients infected with hepatitis or the HI virus, for example, into the blood system of the injured person.

Therefore it is desirable to equip such medical devices with protective mechanisms, which offer protection from injury.

The following requirements exist for such protective mechanisms:
- An accidental collision between point, needle and/or blade and user (injury caused by sticking or cutting) must be precluded.
- The hands must always remain behind the point, needle and/or blade.
- The protective mechanism should be an integral part of the device that has the point, needle and/or blade.
- It should be effective both before and shortly after use of the device (an injection, for example), and during the disposal process (waste).
- Protective mechanisms should be easy to use, without instructions, and in an ideal case should function automatically and be operated with one hand.
- During use of the device (an injection, for example), in other words while the protection is necessarily deactivated, the protective mechanism is not allowed to be in the way of the user.
- It should give clear visual indication of its status (protection in effect/not in effect).
- Its activation should ideally be structured to be irreversible, so that the protection cannot be cancelled out.
- The protective mechanism should be reliable and environmentally friendly, as well as inexpensive.

A plurality of mechanisms is known for protection from sharp needles, which mechanisms are a more or less ideal implementation of the above demands. For example, U.S. Pat. No. 4,735,618 and U.S. Pat. No. 6,796,968 disclose needle sheaths that are pushed over the needle after an injection has been administered, using hinge joint mechanisms. U.S. Pat. No. 5,879,337 describes a needle cap that is pushed along the needle, sliding to the point, and held using a holder thread, in such a manner that it does not slip off the needle point. Spring elements are described here, as well.

The protective mechanisms are usually simple mechanical systems composed of plastic injection-molded parts and, if necessary, spring elements, which are not a hindrance during the injection, but can be activated with simple triggering principles after the injection, and from then on surround sharp needles in protective manner.

The protective devices can already be integrated into syringes or cannulas, or can be additional parts that can subsequently be attached to cannulas or syringes.

Aside from devices that can simply be pushed, flipped, or clamped by hand, more convenient syringe protectors are also known, which are automatically triggered at the end of an injection (syringe piston in the end position) and bring the cannulas into a secured position or bring a protective tube into a barrier position.

The major disadvantage of the known syringe protectors is their mechanical complexity and material properties, which result in significant additional costs for the syringe body.

Another disadvantage of the known syringe protectors is that these must usually be connected with the syringe or cannula subsequently, in other words they require an additional production step.

It is therefore the task of the invention to make available protective mechanisms that function simply and reliably, and are made from inexpensive materials. A second task consists in making available protective mechanisms that do not have to be connected with the device that has a syringe, needle, or other pointed or sharp objects, in a separate method step.

The task of the invention is accomplished by means of a method in which the actual protective device is connected with the device that has a syringe, needle, or other pointed or sharp objects, using a film. This film can be an identification label that is required to identify the device, in each instance, in any case, so that the labeling process simultaneously represents the process of equipping the device with the protective mechanism.

The invention further proposes to structure the protective device itself from film materials that are processed in continuous methods.

By means of the methods described above, such protective mechanisms can be produced inexpensively and precisely. The invention furthermore also comprises a protective mechanism that contains at least one film, as well as an arrangement of protective mechanisms, and a device connected with the protective mechanisms.

In the following, film shall be understood to mean any kind of roll-shaped material webs or pieces produced from them. Aside from plastic webs, this also includes other flat, rolled-up materials, such as paper webs or thin metal foils. Connection is understood to mean affixation that takes place by gluing, preferably adhesive gluing, or by means of physical or chemical methods. The latter category primarily includes welding, soldering, or shrink-fitting, both over the full area and partially.

Furthermore, in the following, the term "needle" will be used, for the sake of simplicity, to mean any kind of pointed or sharp objects. This primarily includes syringe needles, infusion needles, acupuncture needles, cannulas, lancets, blades, and scalpels.

The present invention includes an assembly or a combination of the protective mechanism and a syringe having a syringe body and needle that poses a risk of injury.

The numerous embodiments of the invention will be explained in greater detail in the following, using the figures. All of the figures are to be understood as being not to scale, but rather schematic. Specifically, the layer thicknesses of individual film layers are shown greatly enlarged, for reasons of a clear illustration.

Figure 2:
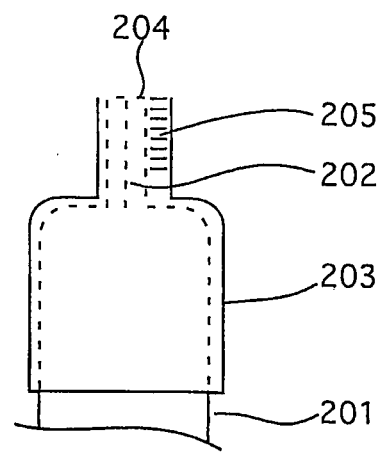
Figure 3:
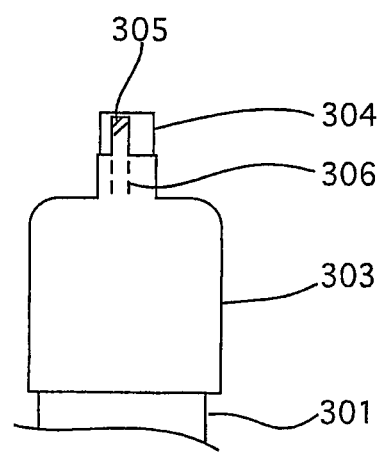
Figure 4:
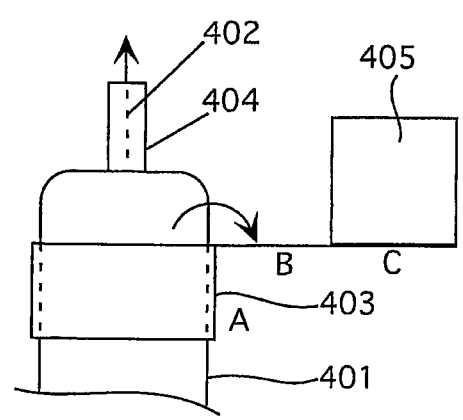
Figure 5:
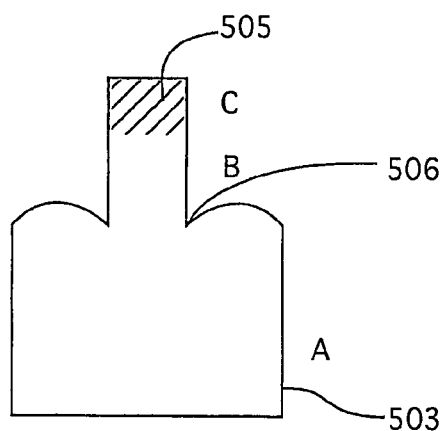
Figure 6:
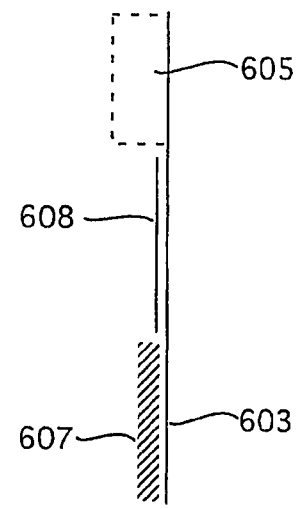
Figure 7:
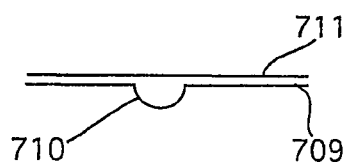
Figure 8:
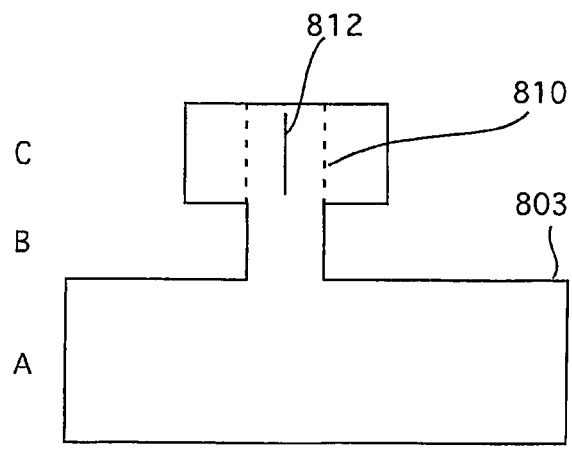

The figures show:

FIG. 1 a protective mechanism according to the invention, connected with a syringe body, in a side view, FIG. 2 another embodiment of a protective mechanism according to the invention, connected with a syringe body, in a side view, FIG. 3 a variant of the embodiment from FIG. 2, FIG. 4 a protective mechanism according to the invention, connected with a syringe body and folded open, in a side view, FIG. 5 a specific embodiment of the protective mechanism according to the invention, in a top view, FIG. 6 another specific embodiment of the protective mechanism according to the invention, in a side sectional view, FIG. 7 a view from above into a preferred embodiment of the protective device of the protective mechanism according to the invention, FIG. 8 a front view of a particularly preferred embodiment of the protective mechanism, with inlet slitting, FIG. 9 *a-d* various forms of the inlet slitting according to FIG. 8, FIG. 10 a view from above into another preferred embodiment of the protective device of the protective mechanism according to the invention, FIG. 11 a side view of such a preferred embodiment of the protective device of the protective mechanism according to the invention.

FIG. 1 shows a syringe body 101 that has a needle 102 (shown with a broken line in the covered regions). A protective mechanism 103 according to the invention is affixed to the body in a region A. This mechanism consists of three essential regions: The connection region A, the bridging region B, and the region of the protective device C. The protective device serves to protect users of the syringe from injuries after administration of the injection. It can be configured both as a film and as a hard plastic part or similar component. Precise embodiments of the protective device are explained in the dependent claims. It is decisive for the invention that at least the region A of the protective mechanism is configured as a film. This film serves for affixing the entire mechanism to the syringe and can, in addition, serve for identification purposes. In this case, it is configured as a label. A first preferred embodiment of this film is to configure it as a self-adhesive film, so that it can be directly glued onto the syringe or similar device. Permanently adhering adhesives are particularly preferred, in this connection, which are not water-soluble, in order to guarantee a water bath resistance, which is often required in the case of pharmaceutical applications. Polyethylene terephthalate (PET) or polyolefins (polyester—PE, polypropylene—PP, or polyvinyl chloride—PVC) have proven themselves to be particularly advantageous starting materials for the film.

FIG. 2 shows another possibility of fixation: Here, the regions A, B, and C from FIG. 1 are covered with a film part, to their full extent, which part has a protective device 205 in the region of the needle 202. This figure shows the syringe 201 together with the protective mechanism 203 before administration of an injection, i.e. in the unopened state. Therefore the needle 202 is surrounded by a protective cap 204, which is also sheathed by the film of the protective mechanism. The protective mechanism therefore mantles the syringe body almost completely, all the way to the upper end of the syringe cap. The film of the protective mechanism is therefore preferably configured in the manner of a tube, as a so-called shrink film. Such shrink tubes (sleeve labels) can be applied to objects such as this syringe body by means of applying heat or by means of stretching them and fitting them over the object. In this connection, the film contracts in such a manner that it lies against the mantled body over its entire area.

In this case, the protective device 205 consists of a comb-like or feeler-like arrangement, which can engage around the exposed needle after administration of the injection. Preferably, there are thickened regions at the ends of this "comb" towards the syringe, which allow engagement of the needle, similar to the manner of a hook-and-loop closure.

An advantage of the shrink-fit embodiment of the invention can be seen in FIG. 3. Again, a protective mechanism like 303 in FIG. 2 is applied to the syringe body 301. In the drawing, the broken-line indication of the outline of the syringe body was left out, for reasons of a better illustration. In the region of the needle protection cap 304, the film of the protective mechanism (affixed only on part of the area here) has a perforation 306, which makes it possible to pull the film off in this region and thereby to provide proof that the syringe has been opened. Tearing open is facilitated in that the protective device 305 is also affixed on the underside of the film in the region of the perforation 306. It serves as a grabbing aid for opening along the perforation. Similar proof of having been opened can also be implemented in the case of self-adhesive embodiments of the protective mechanism. In this case, the needle protection cap would be mantled by a self-adhesive film that either also has a tear-open perforation or proof of having been opened, for example, in the form of the so-called VOID effect. This brings about the formation of an irreversibly generated line of writing or symbol of printed ink in the opened region.

FIG. 4 shows a protective mechanism according to the invention in a side view, on a syringe body, in the folded-open state: The syringe body 401 is shown, which has a needle protection cap 404, which protects a needle 402 (shown with a broken line) before administration of the injection. The protective mechanism 403 with the protective device 405 is folded away from the protective cap at a 90 degree angle, so that the cap can now be removed and the injection can be administered. After administration, the protective mechanism is folded back again, so that the protective device accommodates the needle and protects the user from injury. In order to guarantee administration of the injection without hindrance for the user, it is necessary for the mechanism to fold over simply and in defined manner in the transition region between A and B. In order to guarantee this, various measures can be taken in this transition region.

FIG. 5 shows a protective mechanism 503 with a protective device 505, not shown in greater detail, identified with cross-hatching, for needles, in which a punching 506 was made in the transition region between A and B. By means of this punching, the region B folds over in defined manner, due to the bending of the transition region predetermined by the cylinder shape, when the protective mechanism is applied to a cylindrical or cylinder-like device.

A similar effect can be achieved by means of the structure in FIG. 6, in which a protective mechanism 603 with a protective device 605, not shown in greater detail, and an adhesive layer 607 (for fixation on the object) is shown. In the bridging region B, an additional film 608 is affixed, which reinforces this region and thus leads to weakening of the film in the transition region between A and B. In place of an additional film, it is also possible to use a part of the protective device (which is injection-molded, for example), which part comes to an end in a downward direction, as a reinforcement. Weakening of this transition region can also be achieved in that an embossing or a reduction in the width of the bridging region is provided there.

In general, the effect of defined folding is achieved by means of increased material rigidity in the transition region A and/or weakening in the transition region between bridging region and connection region. Preferably, both measures are used in a suitable combination, in order to achieve a precisely defined folding effect in their interaction.

In the following figures, particularly preferred embodiments of the actual protective device of the protective mechanism will now be discussed. Fundamentally, the protective device can also be formed from at least one film or from another part, usually one made from plastic.

FIG. 7 shows a particularly preferred variant of a film part in a view from above. A first film 709 is deformed, in a region 710, in such a manner that a needle can be introduced into the convexity. In order to surround this object from all sides, a second film 711 is usually applied to the back of the film. The needle or another object to be protected is introduced into the cavity between them, usually through a slitting in one of the two films 709 or 711.

A special form of this film part consists in the fact that the convexity is configured as a double convexity in the region 710. Other shapes of the convexity are also possible, and advantageously correspond with the shape of the object to be protected.

FIG. 8 shows a corresponding protective mechanism 803 in a front view. The region of the convexity 810 is shown with a broken line here. In this figure, the slitting 812 can also be seen, into which the needle is introduced.

It can prove to be practical to make the slitting not in a straight shape, as shown in FIGS. 9 *a-d*. 9*a* shows a slitting that runs at a slant, not perpendicular to the edge of the film; 9*b* shows a wave-shaped progression; 9*c* shows a zigzag line; and 9*d* shows a crenellated progression. In this way, it can be guaranteed that while somewhat greater effort is required to place the object to be protected into the cavity behind the slitting, it is more difficult for the object to escape again. Specifically, this applies if the film is deformed after introduction of the slitting (shrunk or rotated in itself, for example), and thereby an excess length of the film regions produced by the slitting is formed.

As indicated, non-film-like parts can also be used alternatively to the protective devices presented, which consist of one or more films. Primarily, these are injection-molded parts, or parts produced from extruded profiles. A possible shape of such a molded part is shown in a view from above in FIG. 10. Here again, analogous to the slitting in the previous examples, an inlet is made available for the needle. Numerous shapes are possible for such protective devices; they can be based on the known state of the art, as well. The absorption of fluids, specifically potentially infected bodily fluids, can be additionally guaranteed by the use of moisture-absorbing materials such as woven or nonwoven textiles. Polystyrene (PS), acryl nitrile butadiene styrene (ABS), polycarbonate (PC), and thermoplastic urethane (TPU) have primarily proven to be suitable materials for injection-molded parts, or parts produced from extruded profiles.

FIG. 11 shows such a protective device in a side view. In the region in which the needle is supposed to be accommodated—shown on the right here—the profile is configured to be larger, in order to make sufficient room available for the needle. In the region that primarily comes to rest in the bridging region B, and which is connected with the film of the protective mechanism, the thickness of the protective device can be clearly less. As described above, it can serve to reinforce the film and thereby to guarantee a defined folding mechanism.

The usual embodiment of the present invention consists in making at least part of the film region available as a label, i.e. as an imprinted film, since in this way, a process step can be saved in making syringes or other devices available: Application of the protective mechanism is labeling, at the same time. The imprinting can particularly relate to the use of the protective mechanism. In addition to a pure identification function, labels can contain other functional characteristics, which can also be used in the case of the present invention: For example, it is possible to equip the label with removable self-adhesive documentation parts that are pasted into a patient's file, as proof, after administration of an injection. Also, the integration of film-like hanging devices is possible, or of a region whose surface is treated in such a manner that it can be imprinted by means of subsequent writing methods even after the protective mechanism is made available by the manufacturer.

Protective mechanisms according to the invention, as described here, are usually connected with the devices for which they are intended in automated dispensing or application methods. For this purpose, it is particularly practical and lowers costs to make the mechanisms available and apply them in an endless method. According to the invention, the protective mechanisms are therefore connected with one another directly or indirectly. This usually takes place, in the case of the tube-like embodiments (sleeve technology), in that the individual tubes are supplied lined up behind one another in endless manner, possibly separated by means of perforations or other weakenings, and only completely separated from one another when the tube is applied to the devices, for example cut off or separated at the weakening lines. In the case of self-adhesive solutions, on the other hand, it is practical to dispose the protective mechanisms on a carrier web, whereby it is particularly practical, for production and disposition reasons, to dispose the region of the protective device perpendicular to the web running direction. In this connection, the region of the protective device usually stands farther away from the carrier than the remaining region, and for this reason, a recess in the carrier web can be provided here, to save height. In this way, the protective mechanisms on the carrier web can be more easily rolled up into a roll. A particular form of rolling up consists in making the protective mechanisms on their carrier web available in a dispensing cassette, a dispenser. In this connection, the protective mechanisms are held in the cassette, and specifically during dispensing, in such manner that they can be rolled up and dispensed without complications, despite the thickness differences due to the protective mechanism. Furthermore, it is particularly advantageous to use a particularly thick carrier paper, in order to avoid any interaction of the various layers of protective mechanisms that lie on top of one another, in the rolled-up state.

The invention claimed is:

1. An assembly comprising a protective mechanism and a syringe having a syringe body and a needle that poses a risk of injury, the protective mechanism comprising:
   a connection region, the connection region being formed from at least one film and being attached to the syringe, the at least one film being a self-adhesive film to glue the at least one film directly on the syringe body by said self-adhesive;

a protective device, the protective device providing protection from injury and to accommodate the needle, the protective device being configured as a hard plastic part;

a bridging region disposed between the connection region and the protective device; and a weakening at a transition between the connection region and the bridging region to allow defined folding over of the bridging region to allow folding the protective device away from the needle in an operational state and then to allow folding the protective device back to accommodate the needle in another operational state; and wherein the adhesive of the self-adhesive film is present only on part of an area of the film on the syringe body; and wherein the weakening is a punching or a slitting at the transition between the two regions; and further comprising a reinforcement in thickness, the reinforcement in thickness and the weakening being coordinated with one another, in terms of their effect, such that the defined folding over is made possible; and wherein the reinforcement in thickness is formed as an additional film of at least the bridging region.

2. The assembly according to claim 1, wherein the at least one film is produced from polyethylene terephthalate, polyester, polypropylene, or polyvinyl chloride.

3. The assembly according to claim 1, wherein the at least one film has means for tearing open in a state in which the at least one film is applied to the syringe body.

4. The assembly according to claim 3, wherein the means for tearing open are a perforation.

5. The assembly according to claim 3, wherein the means for tearing open are an embossing.

6. The assembly according to claim 3, wherein the means for tearing open are a punching.

7. The assembly according to claim 3, wherein the means for tearing open lie in a region in which the at least one film comes to lie in a region of the needle that poses a risk of injury, in the state in which the at least one film is applied to the syringe body.

8. The assembly according to claim 7, wherein the means for tearing open allow a part of the at least one film to be removed in the region in which the at least one film comes to lie in the region of the needle that poses a risk of injury, in the state in which the at least one film is applied to the syringe body.

9. The assembly according to claim 1, wherein the adhesive is not soluble in water.

10. The assembly according to claim 1, wherein the adhesive is a permanently-adhering adhesive.

11. The assembly according to claim 1, wherein the adhesive is applied only to part of the area.

12. The assembly according to claim 1, wherein the adhesive is treated, on part of the area, with means for weakening or canceling out the adhesive.

13. The assembly according to claim 1, wherein the at least one film has at least one other functional part.

14. The assembly according to claim 13, wherein the at least one other functional part is at least one removable item of documentation.

15. The assembly according to claim 13, wherein the at least one other functional part is at least one hanging device.

16. The assembly according to claim 1, wherein the at least one film has an imprinting.

17. The assembly according to claim 16, wherein the imprinting represents information for use of the protective mechanism.

18. The assembly according to claim 1, wherein the at least one film has a region that is imprinted.

19. The assembly according to claim 1, wherein the protective device is a functional part attached at least to the bridging region.

20. The assembly according to claim 19, wherein the functional part is a film.

21. The assembly according to claim 20, wherein the functional part is a deformed film.

22. The assembly according to claim 21, wherein the functional part is a deep-drawn film.

23. The assembly according to claim 22, wherein the deep-drawn film is covered, at least over part of its area, by another film.

24. The assembly according to claim 22, wherein the deep-drawn film has a slitting.

25. The assembly according to claim 24, wherein the slitting of the deep-drawn film ends not perpendicular to an edge of the deep-drawn film.

26. The assembly according to claim 25, wherein the slitting of the deep-drawn film runs in a wave shape.

27. The assembly according to claim 25, wherein the slitting of the deep-drawn film runs in a zigzag shape or a crenellated shape.

28. The assembly according to claim 24, wherein film regions produced by the slitting of the deep-drawn film overlap after the slitting of the deep-drawn film.

29. The assembly according to claim 22, wherein the deep-drawn film is shrunk.

30. The assembly according to claim 19, wherein the functional part is an injection-molded part.

31. The assembly according to claim 30, wherein the functional part is a part made from polystyrene, polypropylene, acryl nitrile butadiene styrene, or thermoplastic urethane.

32. The assembly according to claim 19, wherein the functional part is a part produced from an extruded profile.

33. The assembly according to claim 19, wherein the functional part is a comb-like component or a feeler-like component.

34. The assembly according to claim 1, wherein the weakening at the transition between the two regions is an embossing.

35. The assembly according to claim 1, wherein the weakening at the transition between the two regions is a reduction in a width of the bridging region.

36. The assembly according to claim 1, wherein the protective mechanism has a moisture-absorbing material.

37. The assembly according to claim 1, wherein the protective device completely releases the needle when folding the protective device away from the needle in the operational state.

38. An assembly comprising a protective mechanism and a syringe having a syringe body and a needle that poses a risk of injury, the protective mechanism comprising:

a connection region, the connection region being formed from at least one film and being attached to the syringe, the at least one film being a self-adhesive film to glue the at least one film directly on the syringe body by said self-adhesive;

a protective device, the protective device providing protection from injury and to accommodate the needle, the protective device being configured as a film;

a bridging region disposed between the connection region and the protective device; and a weakening at a transition between the connection region and the bridging region to allow defined folding over of the bridging region to allow folding the protective device away from the needle in an operational state and then to allow folding the protective device back to accommodate the needle in another operational state; and wherein the bridging region is configured as a film and wherein all three films are integrally formed;

wherein the weakening is a punching or a slitting at the transition between the two regions; and further comprising a reinforcement in thickness the reinforcement in thickness and the weakening being coordinated with one another, in terms of their effect, such that the defined folding over is made possible; and wherein the reinforcement in thickness is formed as an additional film of at least the bridging region.

39. An assembly comprising a protective mechanism and a syringe having a syringe body and a needle that poses a risk of injury, the needle having a proximal end connected to the syringe body and a distal end and a portion between the proximal end and the distal end, the protective mechanism comprising:

a connection region, the connection region being formed from at least one film and being attached to the syringe, the at least one film being a self-adhesive film to glue the at least one film directly on the syringe body by said self-adhesive;

a protective device, the protective device providing protection from injury and to accommodate the needle including the proximal and distal ends of the needle and the portion between the proximal end and the distal end, the protective device being configured as a hard plastic part;

a bridging region disposed between the connection region and the protective device; and a weakening at a transition between the connection region and the bridging region to allow defined folding over of the bridging region to allow folding the protective device away from the needle and from the proximal and distal ends of the needle and the portion between the proximal end and the distal end in an operational state and then to allow folding the protective device back to accommodate the needle in another operational state; and wherein the adhesive of the self-adhesive film is present only on part of an area of the film on the syringe body; and wherein the weakening is a punching or a slitting at the transition between the two regions; and further comprising a reinforcement in thickness, the reinforcement in thickness and the weakening being coordinated with one another, in terms of their effect, such that the defined folding over is made possible; and wherein the reinforcement in thickness is formed as an additional film of at least the bridging region.

40. An arrangement of protective mechanisms, each protective mechanism being capable of being used in combination with a syringe having a syringe body and a needle that poses a risk of injury and comprising:

a connection region formed from at least one film and capable of being attached to said syringe, the at least one film being a self-adhesive film to glue the at least one film directly on the syringe body by said self-adhesive, a protective device configured as a hard plastic part providing protection from injury and to accommodate the needle, a bridging region disposed between the connection region and the protective device, and a weakening at a transition between the connection region and the bridging region to allow defined folding over of the bridging region to allow folding the protective device away from the needle in an operational state and then to allow folding the protective device back to accommodate the needle in another operational state, wherein the protective mechanisms are directly or indirectly connected with one another; and wherein the adhesive of the self-adhesive film is present only on part of an area of the film on the syringe body;

wherein the weakening is a punching or a slitting at the transition between the two regions; and further comprising a reinforcement in thickness the reinforcement in thickness and the weakening being coordinated with one another, in terms of their effect, such that the defined folding over is made possible; and wherein the reinforcement in thickness is formed as an additional film of at least the bridging region.

41. The arrangement according to claim 40, wherein the protective mechanisms are disposed behind one another in the shape of a tube.

42. The arrangement according to claim 41, wherein the individual protective mechanisms are separated by one another by weakenings of the tube.

43. The arrangement according to claim 42, wherein the weakenings of the tube are perforation punchings.

44. The arrangement according to claim 40, wherein the protective mechanisms are disposed adhering on a carrier web.

45. The arrangement according to claim 44, wherein each protective device comes to lie perpendicular to a web running direction.

46. The arrangement according to claim 44, wherein a recess of the carrier web is provided in a region of the protective devices.

* * * * *